United States Patent

Brigalia, Sr. et al.

[11] Patent Number: 5,878,526
[45] Date of Patent: Mar. 9, 1999

[54] SCENT DISPENSING ELECTRONIC BUG KILLER DEVICE

[76] Inventors: Roger A. Brigalia, Sr., 27350 Intracostal Rd., Unit B, Plaquemine, La. 70764; Arthur S. Hardy, 7180 S. River Rd., #22, Addis, La. 70710

[21] Appl. No.: 12,088

[22] Filed: Jan. 22, 1998

[51] Int. Cl.⁶ .................................................. A01M 1/22
[52] U.S. Cl. .................................................. 43/112
[58] Field of Search ................................ 43/98, 112, 121

[56] References Cited

U.S. PATENT DOCUMENTS

| | | | |
|---|---|---|---|
| 4,037,351 | 7/1977 | Springer | 43/112 |
| 4,423,564 | 1/1984 | Davies et al. | 43/121 |
| 4,709,502 | 12/1987 | Bierman | 43/112 |
| 4,914,854 | 4/1990 | Zhou et al. | 43/112 |
| 5,095,647 | 3/1992 | Zobele et al. | 43/125 |
| 5,168,654 | 12/1992 | Chien | 43/129 |
| 5,241,779 | 9/1993 | Lee | 43/139 |
| 5,282,334 | 2/1994 | Kimura et al. | 43/125 |
| 5,335,446 | 8/1994 | Shigetoyo | 43/125 |

*Primary Examiner*—Thomas Price
*Attorney, Agent, or Firm*—Henderson & Sturm

[57] ABSTRACT

A scent dispensing electronic bug killer device 10 including a housing member 20 having at least one opening 22, an electrical grid member 30, and a bait holder 40 disposed within the housing member 20 and a fan element 43 for forcibly dispersing the scent from the bait holder 40 through the opening 22 to lure roaches 50 into contact with the electrical grid member 30.

8 Claims, 2 Drawing Sheets

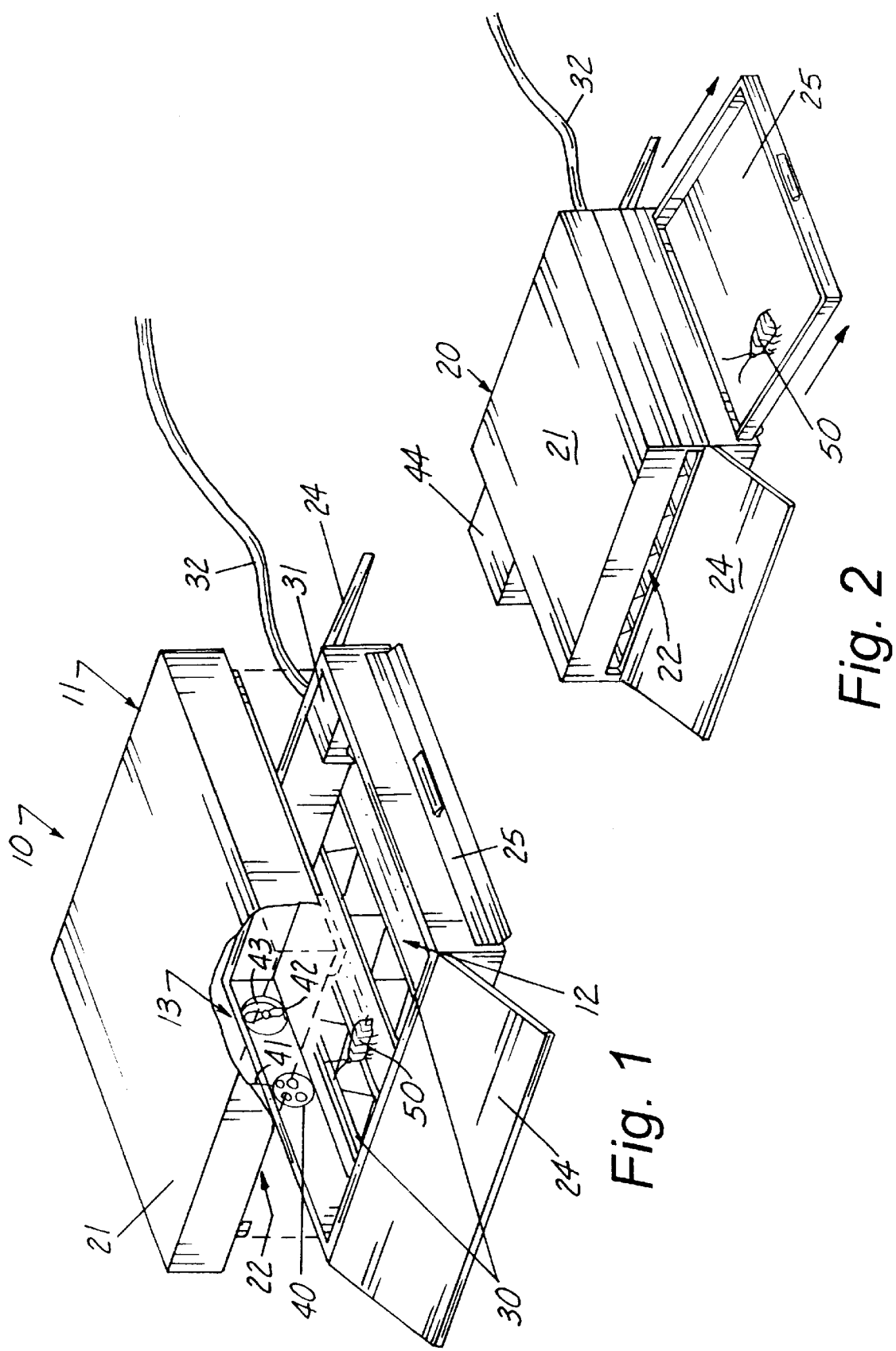

SCENT DISPENSING ELECTRONIC BUG KILLER DEVICE

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of insect control devices in general, and in particular to an electronic bug killer that has a forced air scent dispensing feature.

2. Description of Related Art

As can be seen by reference to the following U.S. Pat. Nos. 5,095,647; 5,168,654; 5,282,334; and 5,335,446, the prior art is replete with myriad and diverse insect control devices.

While all of the aforementioned prior art constructions are more than adequate for the basic purpose and function for which they have been specifically designed, they are uniformly deficient with respect to their failure to provide a simple, efficient, and practical way to lure insects into a confined space wherein an electrical charge will kill those insects entering into the confined space.

While many simple mechanical bug trapping devices employ a scent lure or attractant to entice insects into a trap, the use of such scent lures in an electronic bug killing environment seems to have been overlooked by the industry as a whole.

As a consequence of the foregoing situation, there has existed a longstanding need for a new and improved type of electronic bug killing device that not only employs a scent lure to attract insects into the killing zone, but also uses forced air to disperse the scent lure over a wide area and the provision of such a construction is a stated objective of the present invention.

BRIEF SUMMARY OF THE INVENTION

Briefly stated, the scent dispensing electronic bug killer device that forms the basis of the present invention comprises in general, a housing unit, an electronic grid unit, and a scent dispensing unit wherein the electronic grid unit and the scent dispensing unit are suspended within the housing unit.

As will be explained in greater detail further on in the specification, the housing unit comprises in general, a low profile housing member that is designed to be unobtrusive and fit under certain appliances and other home furnishings where crawling insects such as ants, roaches, or the like are likely to frequent.

The electronic grid unit is suspended within the housing unit above a removable tray element contained within the housing unit to provide for the hands off disposal of the insect carcasses. The scent dispensing unit is suspended within the housing unit at a location remote from the housing unit opening and further provided with a fan for dispersing the scent attractant over a wide area to entice the insects to enter the housing unit and be electrocuted by the electronic grid unit.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is an exploded perspective view of the scent dispensing electronic bug killing device that forms the basis of the present invention;

FIG. 2 is a perspective view of the bug killer device with the disposal tray element partially removed;

DETAILED DESCRIPTION OF THE INVENTION

Figure 3:
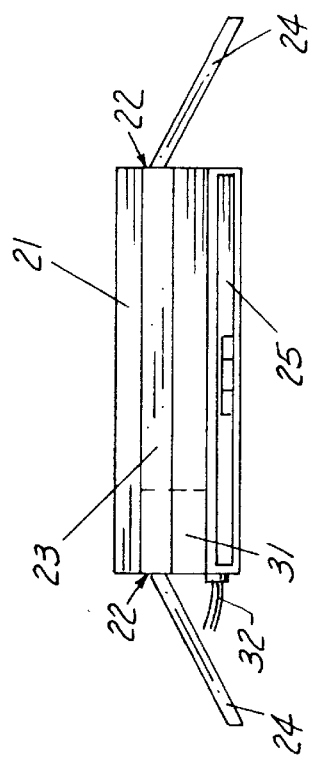
FIG. 3 is a side elevation view of the device.

As can be seen by reference to the drawings, and in particularly to FIG. 1, the scent dispensing electronic bug killing device that forms the basis of the present invention is designated generally by the reference number 10. The bug killing device 10 comprises in general a housing unit 11, an electrical grid unit 12, and a scent dispensing unit 13. These units will now be described in seriatim fashion.

As can best be seen by reference to FIGS. 1 through 3, the housing unit 11 comprises an elongated generally low profile flat rectangular housing member 20 including an upper housing portion 21 provided with a pair of elongated opposed openings 22 whose purpose and function will be described presently.

In addition, the housing member 20 also includes a lower housing portion 23 provided with a pair of ramp elements 24 which cooperate with the opposed openings 22 in the upper housing portion 21 and a removable tray element 25.

Figure 4:
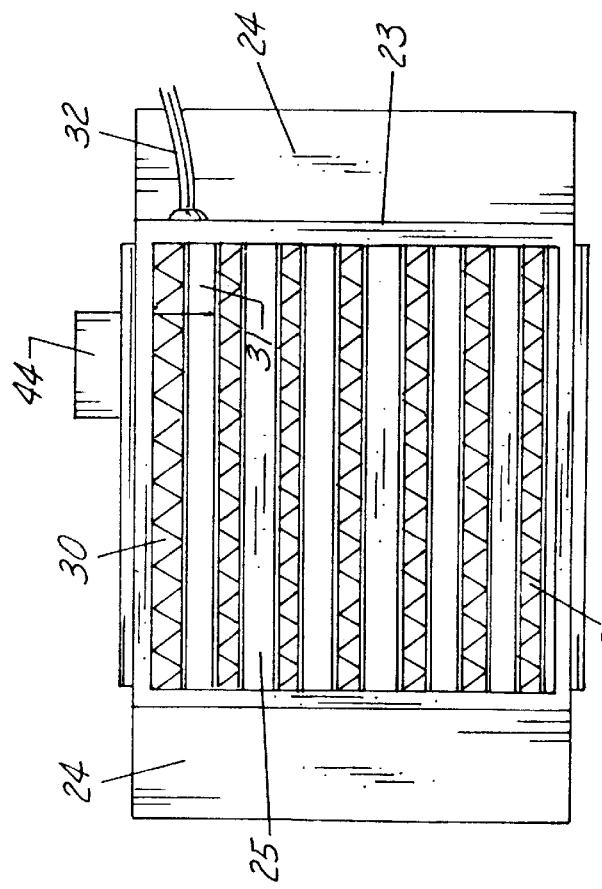
FIG. 4 is a top plan view of the lower portion of the housing unit.

Turning now to FIGS. 1 and 4, it can be seen that the electronic grid unit 12 comprises in general an electrical grid member 30 suspended within the lower housing portion 23 at a location spaced above the removable tray element 25. The grid member 30 is powered by an electrical transformer 31 connected to an electrical power cord 33 in a well recognized fashion.

As can best be seen by reference to FIG. 1, the scent dispensing unit 13 comprises an apertured bait holder 40 suspended by a tether 41 from the roof of the upper housing portion 21 such that the bait holder 40 is positioned slightly above the electrical grid member 30 in the lower housing portion 23.

In addition, the scent dispensing unit 13 also includes a fan element 42 positioned within an aperture 43 in the lower housing portion 23 wherein the fan element 42 is powered by a motor 44 operatively associated with one side of the lower housing portion 23 for dispersing the scent from the suspended bait holder 40 out through the openings 22 on the opposite sides of the housing member 20.

At this juncture, it should be appreciated that the generally slim flat profile of the device 10 coupled with the enlarged flat rectangular upper surface of the housing member 20 allows the device to be placed under kitchen appliances such as toasters, and small microwave ovens where roaches are attracted to spilled crumbs and other food particles.

Furthermore, the forced air dispersal of the scent coming from the bait holder 40 and passing through the openings 22 will prompt the roach 50 to climb up the ramp elements 24 and enter into the housing member 20 in an effort to reach the contents of the bait holder 40. Then upon entering the lower portion 23 of the housing member 20, the roaches 50 will be electrocuted upon coming into contact with the grid member 30.

After a period of time has elapsed, a number of dead roaches will accumulate within the tray element 25 which can be removed from the housing member 20 to effect a hands-off disposal of the dead roaches 50.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooded parts together, whereas, a screw employs a helical surface, in the environment of fastening wooden parts, a nail and a screw may be equivalent structures.

What is claimed is:

1. A scent dispersing electronic bug killer device comprising:

a housing member including an upper housing portion and a lower housing portion defining at least one elongated opening wherein the at least one opening is provided with a ramp element;

an electronic grid member suspended within the lower housing portion beneath said at least one elongated opening;

a scent dispensing unit including a bait holder disposed within said housing member wherein said bait holder is suspended from said upper housing portion; and means for forcibly dispersing the scent from said bait holder through said at least one elongated opening.

2. The device as in claim 1 wherein said housing member is provided with a pair of opposed elongated openings and a pair of ramp elements.

3. The device as in claim 2 wherein the housing member has a generally flat rectangular low profile configuration.

4. The device as in claim 1 wherein said bait holder is disposed within said upper housing portion at a location spaced from said at least one elongated opening.

5. The device as in claim 1 wherein said means for forcibly dispersing the scent from said bait holder through said at least one elongated opening comprises a fan element.

6. The device as in claim 5 wherein said fan element is disposed in the lower portion of the housing member.

7. The device as in claim 1 wherein the lower portion of the housing member is provided with a removably tray element.

8. The device as in claim 7 wherein said removable tray element is disposed beneath said grid member.

* * * * *